(12) United States Patent
Napoles et al.

(10) Patent No.: US 6,403,027 B1
(45) Date of Patent: Jun. 11, 2002

(54) METHOD FOR FUMIGATING PERISHABLES WITHIN A REFRIGERATED CARGO CONTAINER

(76) Inventors: Alexander Elias Napoles, 12845 SW. 49th Ter.; Alexander Alfred Napoles, 12545 SW. 28th St., both of Miami, FL (US) 33175

( * ) Notice: Subject to any disclaimer, the term of this patent is extended or adjusted under 35 U.S.C. 154(b) by 33 days.

(21) Appl. No.: 09/698,332

(22) Filed: Oct. 27, 2000

(51) Int. Cl.$^7$ .............................. A61L 2/00; B01J 19/00
(52) U.S. Cl. ...................... 422/3; 62/78; 422/1; 422/28; 422/32; 422/33; 422/37; 422/40; 426/327; 426/335
(58) Field of Search ............................ 422/1, 3, 28, 32, 422/33, 37, 40; 62/78; 43/125; 426/318, 320, 327, 335

(56) References Cited

U.S. PATENT DOCUMENTS

| 4,234,926 | A | * | 11/1980 | Wallace et al. ................. 700/2 |
| 4,966,755 | A |   | 10/1990 | Smith |
| 5,318,789 | A |   | 6/1994 | Nakagawa et al. |
| 5,662,865 | A |   | 9/1997 | Blatchford |
| 5,678,352 | A |   | 10/1997 | Leitner et al. |
| 6,047,496 | A |   | 4/2000 | Leitner et al. |
| 6,256,905 | B1 | * | 7/2001 | White .......................... 34/218 |
| 6,305,148 | B1 | * | 10/2001 | Bowden et al. ............. 206/386 |

OTHER PUBLICATIONS

U.S. Government, "Chemical Treatments Fumigants Methyl Bromide," PPQ 04/98–01, 1st ed., U.S. Government (USA), p. 2.2.13–48.

* cited by examiner

Primary Examiner—Krisanne Thornton
(74) Attorney, Agent, or Firm—Ruben Alcoba, Esq.

(57) ABSTRACT

A method for fumigation perishables within an existing refrigerated cargo container that does not require the refrigerated cargo container to be tented. The method uses the inherent characteristics of the cargo container to form the fumigation chamber environment. The method insures that the cargo container is fit for fumigation purposes, more specifically, that the refrigerated cargo container does not allow the escape of fumigant beyond the reasonable level allowed by the agency monitoring the fumigation process.

20 Claims, 3 Drawing Sheets

METHOD FOR FUMIGATING PERISHABLES WITHIN A REFRIGERATED CARGO CONTAINER

BACKGROUND

The United States of America requires that imported perishables be inspected for pests upon arrival to U.S. Ports of entry. If pests are detected in the perishables, then the U.S. inspector will determine if the in-coming perishables need to be fumigated before leaving the United States Custom's quarantine areas. The reason for fumigating perishables is to eliminate any pests that the perishables may bring with them from foreign countries.

It is highly desirable that the amount of fumigant being released into our atmosphere during the fumigation of perishables be reduced. Today, there are two common methods of fumigating perishables. The first method requires tenting the cargo containers containing the perishables once the perishables have been taken to a site suitable for fumigation. The second method requires the taking of perishable in a container to a fixed site, unloading the perishable onto the fixed site, then carrying on the fumigation process and lastly, reloading the perishable to the cargo container that brought the perishable to the fixed site.

The first method of fumigation, the tenting, has the inherent disadvantage of having to fumigate a greater amount of cubic footage than would be required if the fumigation process would be carried out inside the cargo carrying container without the tenting. The fumigation of a greater amount of cubic footage in turn releases a greater amount of fumigant to our environment. The United States, through its statutes has stipulated that the amount of the fumigant, if the fumigant is methyl bromide, must be reduced by 50 percent by the year 2000. Another disadvantage that is associated with tenting is that the process can only be carried out when the weather is favorable, that is to say that if the wind is blowing to strong, the tenting should be avoided, for the chances of having the tented environment produce leaks is greatly enhanced. In the same line of thinking, The Plant Protection Quarantine Manual, PPQ 04/98-01 page 2.2.19, states that even in the best conditions, some gas will escape tented enclosures. Yet another disadvantage of tenting the cargo containers is that the sharp angles of the cargo container could tear the tarpaulins used to tent the containers, this would occur to either changes in weather or mishaps, such as the pulling of the tarpaulins due to a physical accident affecting the tented environment.

The second method of fumigation has the following disadvantages. First, by having to transport the perishables from location to location and the loading and unloading at each location, the life of the perishables are shortened due to the changes in temperature that the perishables experience, that is going from a refrigerated environment to one that is not refrigerated and back to a refrigerated environment. Second, it is not unusual to have mishaps in the loading and unloading of the perishables, the spillage of the perishables being fumigated. Thirdly, the amount of time and manpower required to carry out the process due to the loading and unloading is greatly increased, as opposed to just carrying out the fumigation process inside the cargo container.

Today, perishables are being fumigated with methyl bromide prior to being released from customs. Methyl bromide is a fumigant that is effective in eradicating pests that may be lying on perishables entering this country. Methyl bromide is a gas that is highly toxic and is detrimental to our environment, for this reason, the United States wants to phase out the practice of using methyl bromide in this type of fumigations. The problem that the U.S. encounters in phasing out this gas is that to date, methyl bromide is the most effective gas, workable, in eliminating pests from perishables coming into this country. Other chemicals may be used to eradicate pests, but to date methyl bromide has proven to create the least amount of toxic residue to the areas being fumigated, this in turn benefits the people applying the fumigant for they are not exposed to unsafe levels of fumigant. The reason for this is that methyl bromide disperses into the atmosphere at quicker rates than some of the other fumigants currently available for fumigations during the aeration process. The level of residue acceptable of methyl bromide gas after fumigations is five part per million. Information relevant to attempts to address these problems can be found in U.S. Pat. Nos. 6,047,496, 5,678,352, 5,662,865, 5,318,789 and 4,966.755.

U.S. Pat. Nos. 6,047,496 and 5,678,352 address the issue of reducing the amount of toxic agent being released into the environment by providing an improved structural fumigation process of using a non-flammable liquid cryogenic material which is vaporized to function as a carrier for the toxic agent. The patents do not address as how to minimize the area being fumigated nor do they suggest fumigating the perishables in a refrigerated environment.

U.S. Pat. No. 5,662,865 show an apparatus for fumigations with phosphine gas that form a circulatory loop that minimizes the disposal problems associated with phosphine gas. The patent is not geared toward the fumigation of perishables coming into this country, for phosphine gas requires a greater amount of time for the fumigation treatment of perishables to be effective.

U.S. Pat. No. 5,318,789 teaches how to package a commodity in a fumigation container, fumigating the commodity and shipping the commodity in the container. The patent is geared towards keeping fumigated commodities pest free in a sealed container after fumigation has occurred in this country. The patent requires the taking of the containers to chambers to carry out the fumigation. The present invention would conduct the fumigation in the refrigerated cargo container and thereby eliminate the dangers associated with mishaps, such as spills.

U.S. Pat. No. 4,966,755 describes an enclosure device, a tent, that would surround the item(s) being fumigated. The enclosure devise appears to be pieces of materials that are connected to each other so that fumigation can be undertaken inside of said pieces once connected. The device requires one to tent the item(s) to be fumigated.

For the forgoing reasons, there is a need for a method for fumigating perishables within an existing refrigerated cargo container that will reduce the amount of fumigant released into the atmosphere by at least thirty percent, if the fumigation process is carried out in a refrigerated cargo container, while at the same time prolonging the life of the perishables being fumigated. In addition, the method can be performed in weather conditions that would not permit the tenting method.

SUMMARY

The present invention is directed to a method of reducing the amount of fumigant used during the fumigation of perishables and in which the method has the inherent advantage of prolonging the life of the perishable being fumigated. The method comprises of preparing an existing refrigerated cargo container that has already been transported to a site that meets the safety standards for fumigation of perishables. The method is conducted using an existing refrigerated cargo container that has the following physical attributes: two front and two rear drain holes, an air exchanger, a pair of doors that form a seal do to their construction and a refrigeration system. The method commences by first visually checking the outside of the refrigerated cargo container for any signs of damaged areas that may lead to leaks occurring. If damaged areas found, then sealing said damaged areas with a sealant, if possible, if damaged areas prove to be beyond repair, then do not proceed with the aforementioned method. Then placing at least one fan within the refrigerated container, this step can be done at this juncture or at any other juncture so long as one fan is connected to the gas introduction hose prior to the commencement of the fumigation process, the amount of fans required are dependant on the cubic footage of the container or the method of the invention being used. The next step would be to clear two of the drain holes in said refrigerated container. Through one of the drain holes cleared introduce a gas introduction hose, said gas introduction hose would be connected to one of the fans earlier introduced or to the fan earlier introduced, the fan would be positioned to blow the fumigant toward the front or the rear of the refrigerated container so that the fumigant introduced into the container can be dispersed within. Through the other drain hole cleared introduce reading lines and electrical lines for powering the fans or fan within the refrigerated container. The reading lines should be placed in the container according to the placement required by the PPQ manual or any other governmental guidelines for fumigations intact at the time of the fumigation process. After introducing the gas introduction hose, the reading lines and the electrical lines through the above drain holes seal the drain holes with any available commercial sealant that would prevent fumigant leakage. Then, plug the drain holes not cleared with a plugging means that would prevent fumigant leakage from the drain holes not cleared. Prior to conducting the fumigation or any other type of pressure tests, close the air exchanger of the refrigerated container. Then check the temperature of the perishable to be fumigated and determining the dosage of fumigant to be used during the fumigation process. Then, close and secure the doors of said refrigerated cargo container and then commence the fumigation process by releasing the fumigant through the gas introduction hose into said container. While releasing the fumigant into the container check the outside of said container, with a gas or halide detector, for any leaks of the fumigant being used. If leaks are discovered, then seal the areas found to have leaks with any available commercial sealant that seals leaks. After sealing the areas found to have leaks re-check the areas found to have leaks. If leaks are controlled to a satisfactory level, then conduct the fumigation process in the manner and for the period required by the U.S.D.A. or any other governmental agency guidelines for fumigations for the perishables being fumigated. Lastly, aerate the perishables for the required amount of time needed to clear the container of the fumigant. The refrigerated cargo container will not be completely cleared of the fumigant, the guidelines will instruct the fumigators as to how many part per million are required to establish that the fumigant has been aerated to a safe level before the perishables can be released. If for any reason gas leaks cannot be corrected during the fumigation process, then tent the refrigerated cargo container and conduct the fumigation process using the process described in the PPQ manual for fumigation of perishables.

In another embodiment of the invention, the rear drain holes would be used to introduce the gas introduction hose, reading lines and electrical lines and then the rear drain holes would be sealed to prevent gas leakage. The front drain holes would be plugged using any plugging means. If for any reason the rear drain holes cannot be cleared then clear the front drain holes and introduce the gas introduction hose, reading lines and electrical lines through the front drain holes and then the front drain holes would be sealed to prevent gas leakage, then plug the rear drain holes. It is foreseeable that one front drain hole and one rear drain hole may have to be cleared and the remaining drain holes plugged, and that the gas introduction hose and related lines introduced through the cleared drain holes and that said cleared drain holes would then have to be sealed to prevent gas leakage.

In yet another embodiment of the invention, the gas introduction hose, the reading lines and the electrical lines would be introduced through the air exchanger. Then the air exchanger would be sealed using a commercial sealant. All of the drain holes of the refrigerated cargo container would be plugged using plugs or sealant. The fumigation method would be carried out using the same method as above, incorporating the aforementioned steps into the fumigation method.

In another embodiment of the invention, it is foreseeable that a refrigerated cargo container will not have an air exchanger, if this is the case, then the step of closing the air exchanger in the above procedures would be eliminated. The process would be conducted exactly as above, except for the aforementioned step of closing the air exchanger.

In a further embodiment of the invention, the above procedure would be carried out while the refrigeration system of the refrigerated cargo container is running. This embodiment would eliminate the need of extra fans beside the fan required to introduce the fumigant into the refrigerated cargo container. The fan would serve to circulate the fumigant evenly within the cargo container and would prolong the life of the perishable being fumigated.

Another embodiment of the invention would add the further step of conducting a pressure test of said container prior to the commencement of the fumigation process.

Accordingly, it is a principle object of the invention to reduce the amount of fumigant required to fumigate incoming perishables. Because less fumigant is used during the fumigation process, less fumigant is released during the aeration step of the fumigation process, thereby reducing the harm that the fumigant does to our environment.

It is another object of the invention to prolong the life of the perishable being fumigated, this is accomplished by maintaining the perishable refrigerated during the refrigeration process and by exposing the perishable to less fumigant during the initial introduction of the fumigant into the refrigerated cargo container.

It is another object of the invention to reduce spillage associated with having to move a perishable from a cargo container to a fumigation site back onto a cargo container.

Yet another object of the invention is that it allows the perishable to be processed through the custom's quarantine areas at a quicker pace than would be accomplished if having to load and unload the perishables at the fumigation sites or if having to tent the containers carrying the perishables.

Another object of the invention is that the fumigation process can be carried out under weather conditions that would not otherwise permit the fumigation process to be carried out under, such as windy conditions.

These and other objects of the present invention will become readily apparent upon further review of the following specifications and drawings.

DRAWINGS

These and other features, aspects, and advantages of the present invention will become better understood with regard to the following description, appended claims, and accompanying drawings where:

DESCRIPTION

Figure 1:
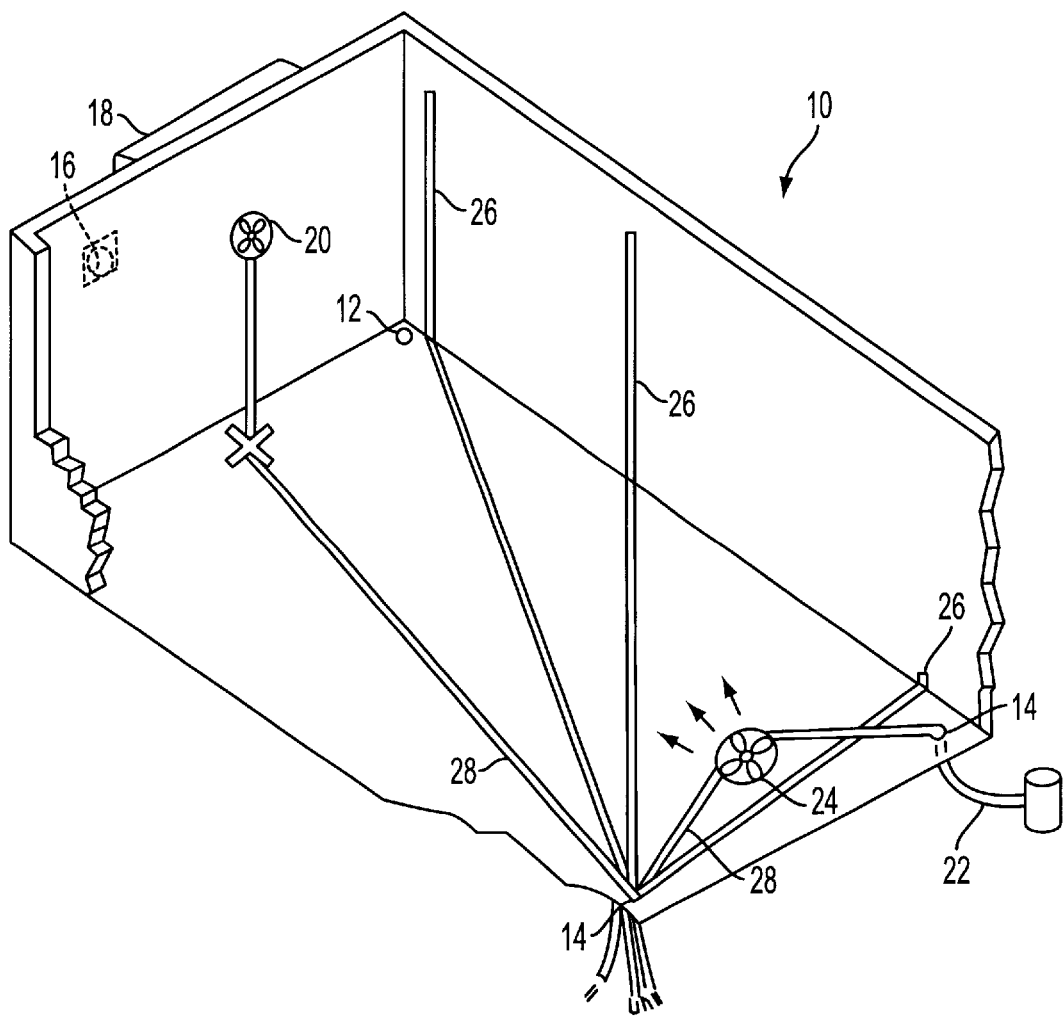
FIG. 1 is an isometric view, containing several cutaways, of an existing refrigerated cargo container that is setup for fumigation using the principles of the present invention.
Figure 2:
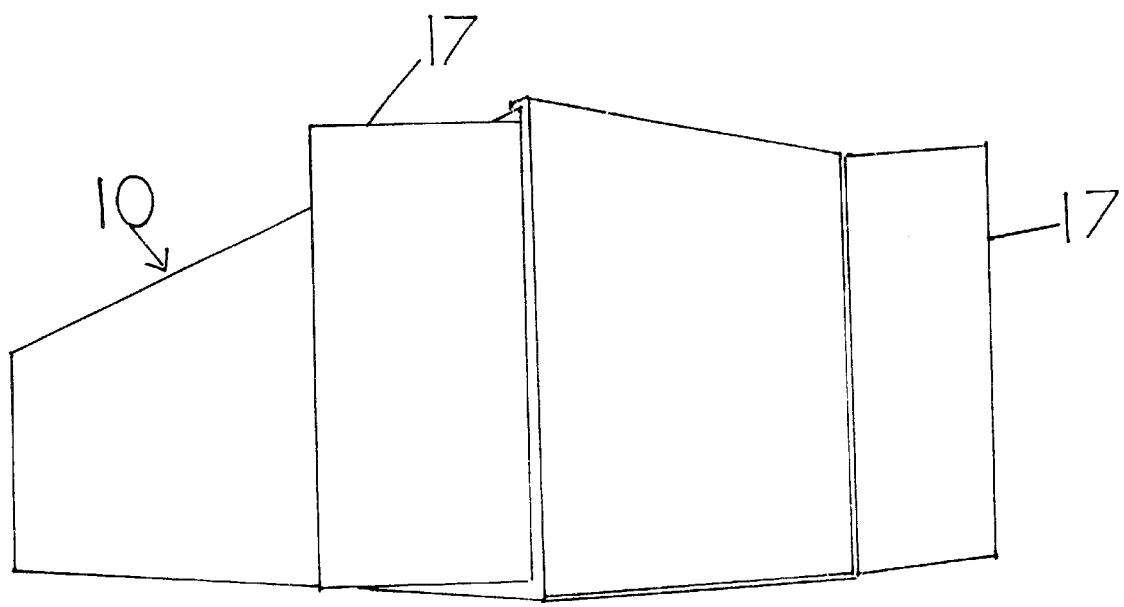
FIG. 2 is a perspective view of an existing refrigerated cargo container that is used to fumigate using the principles of the present invention.

FIG. 1 shows a prepared refrigerated cargo container for the fumigation of perishables, the perishables to be fumigated are not shown in FIG. 1, the perishables would be placed inside of the container according to U.S.D.A. or any other governmental agency guidelines for fumigations prior to conducting the method that follows.

The prepared refrigerated cargo container as shown in FIG. 1 is prepared by a method according to the present invention for fumigating perishables within a refrigerated cargo container 10, wherein said container 10 comprises of a pair of front drain holes 12, a pair of rear drain holes 14, an air exchanger 16, a pair of doors 17 located at the rear of said container 10 and a refrigeration system 18, said method of fumigation comprises the steps of visually checking the outside of said container 10 for any damaged areas; if damaged areas are found, then sealing said damaged areas to prevent fumigant leakage; placing and locating at least one fan 20, 24 within said container; clearing the pair of rear drain holes 14 of said container 10; inserting through one of the cleared rear drain holes 14 a gas introduction hose 22 and then connecting said gas introduction hose 22 to one of the fans 24 earlier placed into the container or to the fan 24 earlier placed into said container 10 and positioning said fan 24 and hose 22 connection so that the fumigant introduced into said container 10 blows towards the front or the rear of said container 10; inserting through the other rear drain hole 14 a plurality of reading lines 26 for measuring the dispersion of fumigant within said container 10 and an electrical line 28 for powering the fan 24 or fans 20, 24 within said container 10; positioning said reading lines 26 within said container 10; then sealing the rear drain holes 14 with a means for sealing the rear drain holes that will prevent fumigant from escaping through the rear drain holes 14; plugging the front drain holes 12 with a means for plugging holes that will prevent fumigant from escaping through the front drain holes 12; closing the air exchanger 16 prior to the fumigation of the perishables; checking the temperature of the perishable to be fumigated; determining the dosage of fumigant to be used to fumigate the perishable; closing and securing the doors 17 of the container 10; releasing the fumigant required to fumigate the perishables through the gas introduction hose 22 into said container 10; checking with a gas or a halide detector the outside of said container 10 for any fumigant leaks; if leaks are discovered, then sealing the areas of the container found to have leaks with a means for sealing the areas found to have leaks; then re-checking the areas of the container that where found to have leaks; if leaks are controlled to an acceptable level, then conducting the fumigation process; and lastly aerating the perishable fumigated for the amount of time needed to clear the container of the fumigant used in the fumigation process.

In the visually checking the container step, the fumigator would walk around the container 10 and look for any dents or gashes on the outside of the container that may identify areas that would allow the fumigant to escape. The fumigator would also check the underside of the container and the top of the container for any of the aforementioned defects. If the fumigator finds any of the aforementioned defects that prove to be beyond correction, the fumigation of perishables according to this process would not be carried out.

If the fumigator identifies damaged areas on the container that can be sealed in the sealing step, then the fumigator would seal the damaged areas by first applying an adhesive to the damaged areas and then taping the damaged areas with a tape that would be resistant to fumigant leakage. The adhesive step above is a precautionary step, the container may be sealed by simply applying tape to the damaged areas.

In the placing of the fans step, the fumigator would place and locate the fans 20, 24 within the container according to the U.S.D.A. or any other governmental agency guidelines for fumigations. The current guidelines for fumigations within a container require the placement of the required amount of fans needed to move a volume in cubic feet per minute equivalent to the total volume of the enclosure in addition to placing within the container a fumigant introduction fan. The fumigant introduction fan 24 has to be placed within the container 10 to introduce the fumigant within the container 10, the fumigant introduction fan 24 would be placed in the front or the rear of the container 10, the rear of the container being the part of the container near the doors 17 of the container 10. The fumigant introduction fan would be placed to blow the fumigant toward the front or the rear of the container 10, depending on the placement of the fumigant introduction fan.

In the clearing of the rear drain holes step, clear the rear drain holes 14 of any drain hoses or any other obstructions so that the drain holes can be free to accept the required lines or hoses that have to be introduced through them.

In the inserting of the gas introduction hose through one of the rear drain holes cleared steps, insert the gas introduction hose 22 through one of the rear drain holes 14 and then connect the hose 22 to the fumigant introduction fan 24. The connection of the hose 22 to the fan 24 should be secured by a clamp or similar attaching mechanism so that the hose does not disconnect from the fan during the fumigation process.

In the inserting of the plurality of reading lines and the electrical lines through the other rear drain hole of the container step, insert the plurality of reading lines 26 and the electrical line 28 through the other rear drain hole 14 of the container 10 and place the reading lines 26 within the container according to the U.S.D.A. or any other governmental agency guidelines for fumigations. Three reading lines 26, also called sampling lines, are currently being placed within a container and the reading lines are located inside of the container as follows; one of the reading lines will be located in the front of the container at a height that is high in relation to the cargo being fumigated, another reading line will be located in the middle of the container at a height that is in the middle in relation to the cargo being fumigated and the last line will be placed at the rear of the container at a height that is low in relation to the cargo being fumigated. There is a gas monitoring lead at the end of each reading line placed within the container 10. The reading lines are introduced into the container to insure that the fumigant is dispersed evenly within the container and also aid in detecting any fumigant leakage. The electrical lines 28 inserted into the container 10 would be connected to the fans 20, 24 previously introduced into the container 10.

In the sealing of the rear drain holes step, seal the rear drain holes 14 of the cargo container by placing and inserting putty in the rear drain holes. One would insert the putty from the interior of the container 10 and from the exterior of the container 10 so that the putty can form a seal surrounding the hose 22, the reading lines 26 and the electrical line 28 that would minimize fumigant leakage through the rear drain holes 14. There are other sealants, that are well know in the art of sealing, that can be used to perform the function that putty is accomplishing in this step.

In the plugging of the front drain holes of the refrigerated cargo container step, the plugging of the front drain holes 12 is accomplished by any number of means. The means can be from inserting a rubber or other malleable material plug that can be manipulated inside of the front drain holes 12 and said plug would form a plug that would minimize fumigant leakage through said front drain holes 12. The plugging material can be caulking strips inserted inside of the drain hole until a seal is formed.

In the closing of the air exchanger step, the air exchanger 16 is manipulated to the closed position. The air exchanger is a vent that is present in most refrigerated cargo containers.

In the checking of the temperature of the perishable step, the perishable's temperature would be checked if possible and if not possible the temperature of the immediate surroundings of the perishable would be checked so that the required amount of fumigant required to fumigate the perishable can be determined. The method of checking the perishable is detailed in the PPQ manual, the Plant Protection and Quarantine Manual.

In the determining the dosage amount fumigant required step, the dosage would be based on the temperature of the perishable to be fumigated and the fumigant used for the fumigation process. The PPQ manual instructs the fumigator as to how to determine the dosage rate that has to be applied to the perishable being fumigated when fumigating with methyl bromide. If fumigating with other fumigants, then one would consult the proper manual to determine the dosage to be used during the fumigation process.

In the closing and securing of the doors step, visually inspect the seals of the doors to insure that the seals are not defective. If the seals are not defective close and secure the doors 17 to form a seal so that the fumigation process can commence. If the seals are suspect, then close the doors 17 and apply adhesive to the areas found to be suspect and then apply a tape that would be resistant to fumigant leakage to the same areas.

In the releasing of the fumigant step, the fumigant will be introduced into the container 10 through the gas introduction hose 22 and the fumigation process will be commenced, the amount of fumigant introduced into the container will be monitored to insure that there is no major leakage of fumigant escaping the container.

In the checking the outside of the container with the gas or the halide step, the fumigator will walk around the container 10 with the gas or the halide detector checking areas suspected to have leaks. The fumigator will also check the underside of the container and the top of the container for leaks.

If leaks are detected, then the fumigator would seal the areas found to have leaks using the procedure used for sealing damaged areas mentioned above. More specifically, first applying an adhesive to the areas found to have leaks and then applying a tape that is resistant to fumigant leakage.

In the re-checking the container 10 with the gas or the halide detector for fumigant leaks step, the fumigator would check the outside of the container found to have leaks for any further fumigant leaks. If fumigant leakage is controlled to a satisfactory level then the fumigation process will be conducted according to the U.S.D.A. or any other governmental agency guidelines for the fumigations of perishables. The fumigation process will be overseen by the government or otherwise empowered inspector overseeing the fumigation procedure and will be conducted for the amount of time required by the U.S.D.A. or any other governmental agency guidelines for the fumigations of perishables. On the other hand, if the leakage of fumigant cannot be controlled to a satisfactory level, then the container will be tented and the fumigation process will be carried out using the old procedure for the fumigation of perishables.

And lastly, in the aerating step, the doors 17 of the container 10 are opened and the perishables are aerated in the manner and for the period required by the U.S.D.A. or any other governmental agency guidelines for fumigations. The perishables will be aerated until the parts per million present in the container are reduced to an acceptable level, the acceptable level of fumigant is determined by the governmental agency overseeing the fumigation procedure. Currently, when aerating a container of methyl bromide, the container will have to be aerated until the concentration of methyl bromide within the container is at most 5 parts per million.

In a variation of the present invention, the drain holes cleared would be the front drain holes and the drain holes plugged would be the rear drain holes. The gas introduction hose, the reading lines and the electrical lines would be inserted through the front drain holes. The sealing and plugging procedures of the drain holes would be conducted as above mentioned, but for the drain holes sealed and plugged would be alternated, more specifically the front drain holes would be sealed and the rear drain holes would be plugged. The remaining steps would be conducted in the same manner as above.

In still a further variation of the present invention, the drain holes cleared may be a combination of one front drain hole and one rear drain hole. The gas introduction hose would either be inserted through one of the cleared front drain holes or one of the cleared rear drain holes and the reading and electrical lines would be inserted through the other cleared drain hole. The sealing and plugging procedures of the drain holes would be conducted as above mentioned, but for the drain holes sealed and plugged would be as follows; the cleared drain holes would be sealed after inserting the gas introduction hose, the reading lines and the electrical lines through them and the remaining drain holes would be plugged. The remaining steps would be conducted in the same manner as above.

In another embodiment of the present invention, the refrigerated cargo container will not have an air exchanger and the step relating to the closing of the air exchanger will be eliminated during the fumigation procedure. The method for fumigating perishables would be conducted in the same manner as above, but for the step of closing the air exchanger.

In another embodiment of the present invention, all of the drain holes in the refrigerated cargo container will be plugged using the aforementioned method for plugging drain holes. The step of clearing the drain holes aforementioned will be eliminated from the process. The gas introduction hose, the reading lines and the electrical lines will be inserted through the air exchanger and placed and connected as above mentioned. The air exchanger will be sealed using a sealing means. The air exchanger will be sealed by placing putty around the gas introduction hose, the reading lines and the electrical lines inserted through the air exchanger until the putty surrounding the hoses and lines form a seal with the body of the air exchanger. The sealing means can be formed by any other materials that have a similar malleability to putty.

In a further embodiment of the aforementioned inventions, the fumigation process would be conducted while running the refrigeration system of the refrigerated cargo container during the fumigation process. It is foreseeable that the amount of fans placed within the container will be reduced using this embodiment of the invention.

Figure 3:
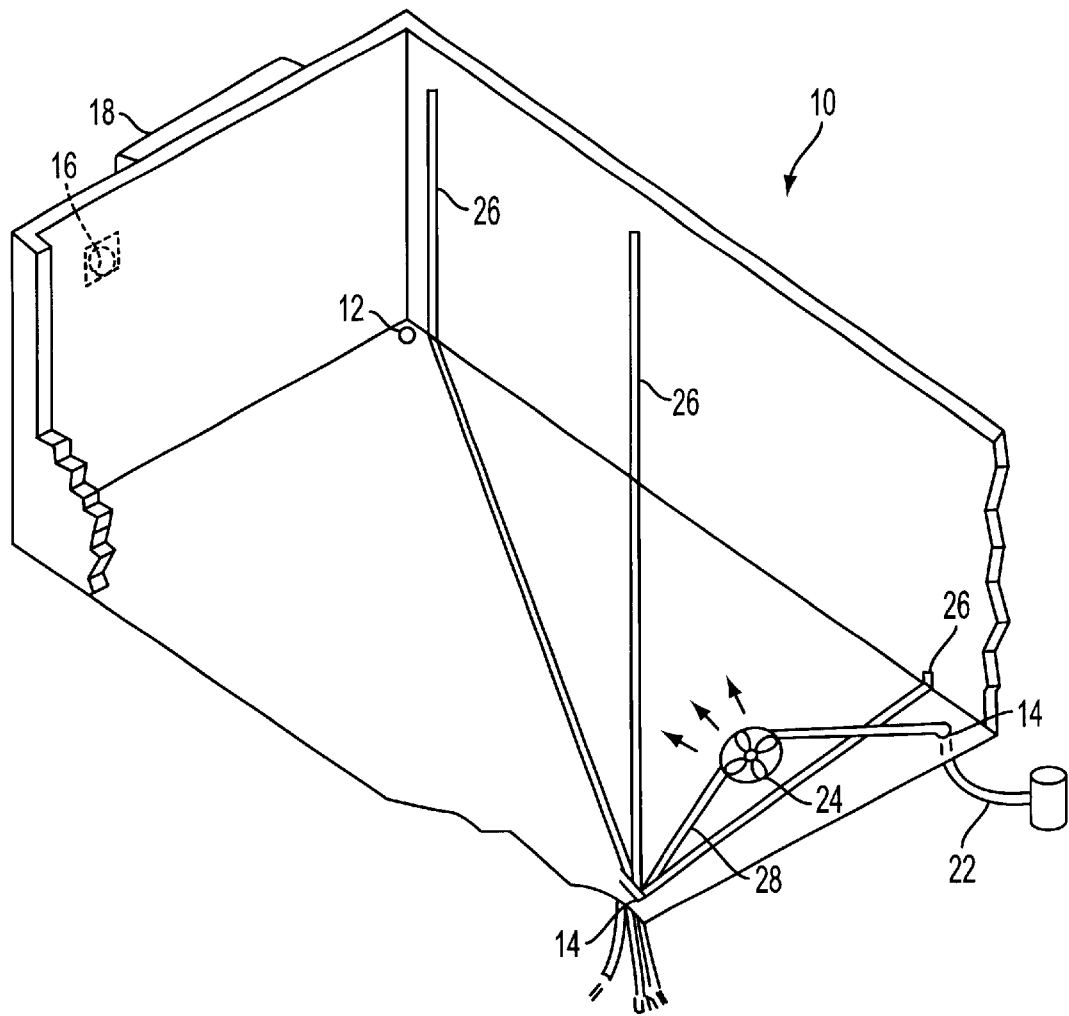
FIG. 3 is another isometric view, containing several cutaways, of an existing refrigerated cargo container that is setup for fumigation using the principles of the present invention.

FIG. 3 shows another embodiment of the present invention. In this embodiment, only one fan 24 is introduced into the container, the fan 24 introduced into the container 10 serves the purpose of introducing the fumigant into the container 10. The refrigeration system 18 would substitute for the amount of fans required to circulate the fumigant within the container 10. The method for fumigating perishables would be conducted in the same manner as above.

In a further embodiment of the aforementioned inventions, a pressure test of the container can be carried out prior to the commencement of the fumigation process after the doors of the container have been closed and secured. Methods of conducting pressure tests are known in the art and will not be discussed further.

The above methods would be used after perishables are inspected for pests upon arrival to U.S. Ports of entry. If pests are detected, then the U.S. inspector will determine if the in-coming perishables need to be fumigated before leaving the United States Custom's quarantine areas. If the inspector decides that the perishables need to be fumigated, the inspector will have the perishables transported to a site for fumigation. The fumigation method will be done outdoors and supervised by a government officer that will monitor the fumigation process. This fumigation method cannot be done on a refrigerated cargo container that is badly damaged, a container that cannot effectively be sealed using the sealing methods previously described.

The previously described versions of the invention have many advantages, including reducing the amount of fumigant required to fumigate incoming perishables. Because less fumigant is used during the fumigation process, less fumigant is released during the aeration step of the fumigation process, thereby reducing the harm that the fumigant does to our environment. Less fumigant is used because the area being fumigated is at least thirty percent smaller than in the old method for fumigating the perishables within the refrigerated cargo container.

Another advantage of the present invention is that it prolongs the life of the perishable being fumigated, this is accomplished by maintaining the perishable refrigerated during the refrigeration process and by exposing the perishable to less fumigant during the initial introduction of the fumigant into the refrigerated cargo container.

Another advantage of the invention is that it reduces spillage that occurs when moving a perishable from a cargo container to a fumigation site back onto a cargo container, this would be the case if using the old method of transporting the cargo to a fixed site, unloading the cargo to the fixed site, tenting the cargo at the fixed site or loading the cargo to a fumigation chamber, fumigating the cargo at the fixed site or chamber and lastly reloading the cargo to the refrigerated container.

Yet another advantage of the present invention is that it allows the perishable to be processed through the custom's quarantine areas at a quicker pace than would be accomplished if having to load and unload the perishables at the fumigation sites or if having to tent the containers carrying the perishables.

Another advantage of the present invention is that the fumigation process can be carried out under weather conditions that would not otherwise permit the fumigation process to be carried out under, such as windy conditions. Windy conditions usually halt fumigation procedures when tenting refrigerated cargo containers.

Although the present invention has been described in considerable detail with reference to certain preferred versions thereof, other versions are possible. Therefore the spirit and scope of the claims should not be limited to the description of the preferred versions contained herein.

What is claimed is:

1. A method for fumigating perishables within a refrigerated cargo container, wherein said refrigerated container comprises of a pair of front and a pair of rear drain holes, an air exchanger, a pair of doors located at the rear of said container, and a refrigeration system, said method for fumigation comprising:

checking said container for any damaged areas;

if damaged areas found, then sealing said damaged areas with a means for sealing said damaged areas;

placing at least one fan within said container;

clearing the pair of rear drain holes of said container;

inserting through one of the rear drain holes a gas introduction hose, then connecting said gas introduction hose to one of the fans earlier placed within said container or to the fan earlier placed in said container;

inserting through the other rear drain hole a plurality of reading lines for measuring the dispersion of fumigant within said container and an electrical line for powering said fans or fan;

positioning said reading lines within said container;

sealing the rear drain holes with a means for sealing the rear drain holes;

plugging the front drain holes with a means for plugging holes;

closing the air exchanger;

checking the temperature of the perishable to be fumigated;

determining the dosage of fumigant to be used in the fumigation process;

closing and securing the doors of the refrigerated cargo container;

releasing the fumigant required to fumigate through the gas introduction hose into said container;

checking with a gas or a halide detector the outside of said container for any fumigant leaks;

if leaks are discovered, then sealing the areas of said container found to have leaks with a means for sealing the areas found to have leaks;

re-checking with the gas or the halide detector the areas of the container that were discovered to have leaks;

if leaks are controlled, then conducting the fumigation process; and lastly, aerating the perishable fumigated for the required amount of time needed to clear the container of the fumigant used in the fumigation process.

2. The method for fumigating perishables within the refrigerated cargo container of claim 1, wherein the refrigerated container is refrigerating the perishable during the fumigation process.

3. The method for fumigating perishables within the refrigerated cargo container of claim 1, which further comprises conducting a pressure test of said refrigerated container prior to the application of the fumigant.

4. The method for fumigating perishables within the refrigerated cargo container of claim 3, wherein the refrigerated container is refrigerating the perishable during the fumigation process.

5. A method for fumigating perishables within a refrigerated cargo container, wherein said refrigerated container comprises of a pair of front and a pair of rear drain holes, an air exchanger, a pair of doors located at the rear of said container, and a refrigeration system, said method for fumigation comprising:

checking said container for any damaged areas;

if damaged areas found, then sealing said damaged areas with a means for sealing said damaged areas;

placing at least one fan within said container;

clearing the pair of front drain holes of said container;

inserting through one of the front drain holes a gas introduction hose, then connecting said gas introduction hose to one of the fans earlier placed within said container or to the fan earlier placed in said container;

inserting through the other front drain hole a plurality of reading lines for measuring the dispersion of fumigant within said container and an electrical line for powering said fans;

positioning said reading lines within said container;

sealing the front drain holes with a means for sealing the front drain holes;

plugging the rear drain holes with a means for plugging holes;

closing the air exchanger;

checking the temperature of the perishable to be fumigated;

determining the dosage of fumigant to be used in the fumigation process;

closing and securing the doors of the refrigerated cargo container;

releasing the fumigant required to fumigate through the gas introduction hose into said container:

checking with a gas or a halide detector the outside of said container for any fumigant leaks;

if leaks are discovered, then sealing the areas of said container found to have leaks with a means for sealing the areas found to have leaks;

re-checking with the gas or the halide detector the areas of the container that were discovered to have leaks;

if leaks are controlled, then conducting the fumigation process; and lastly, aerating the perishable fumigated for the required amount of time needed to clear the container of the fumigant used in the fumigation process.

6. The method for fumigating perishables within the refrigerated cargo container of claim 5, wherein the refrigerated container is refrigerating the perishable during the fumigation process.

7. The method for fumigating perishables within the refrigerated cargo container of claim 5, which further comprises conducting a pressure test of said refrigerated container prior to the application of the fumigant.

8. The method for fumigating perishables within the refrigerated cargo container of claim 7, wherein the refrigerated container is refrigerating the perishable during the fumigation process.

9. A method for fumigating perishables within a refrigerated cargo container, wherein said refrigerated container comprises of a pair of front and a pair of rear drain holes, an air exchanger, a pair of doors located at the rear of said container, and a refrigeration system, said method for fumigation comprising:

checking said container for any damaged areas;

if damaged areas found, then sealing said damaged areas with a means for sealing said damaged areas;

placing at least one fan within said container;

clearing one of the front drain holes and one of the rear drain holes of said container;

inserting through one of the cleared drain holes a gas introduction hose, then connecting said gas introduction hose to one of the fans earlier placed within said container or to the fan earlier placed in said container;

inserting through the other cleared drain hole a plurality of reading lines for measuring the dispersion of fumigant within said container and an electrical line for powering said fans;

positioning said reading lines within said container;

sealing the cleared drain holes with a means for sealing the cleared drain holes;

plugging the remaining drain holes with a means for plugging holes;

closing the air exchanger;

checking the temperature of the perishable to be fumigated;

determining the dosage of fumigant to be used in the fumigation process;

closing and securing the doors of the refrigerated cargo container;

releasing the fumigant required to fumigate through the gas introduction hose into said container;

checking with a gas or a halide detector the outside of said container for any fumigant leaks;

if leaks are discovered, then sealing the areas of said container found to have leaks with a means for sealing the areas found to have leaks;

re-checking with the gas or the halide detector the areas of the container that were discovered to have leaks;

if leaks are controlled, then conducting the fumigation process; and lastly, aerating the perishable fumigated for the required amount of time needed to clear the container of the fumigant used in the fumigation process.

10. The method for fumigating perishables within the refrigerated cargo container of claim 9, wherein the refrigerated container is refrigerating the perishable during the fumigation process.

11. The method for fumigating perishables within the refrigerated cargo container of claim 9, which further comprises conducting a pressure test of said refrigerated container prior to the application of the fumigant.

12. The method for fumigating perishables within the refrigerated cargo container of claim 11, wherein the refrigerated container is refrigerating the perishable during the fumigation process.

13. A method for fumigating perishables within a refrigerated cargo container, wherein said refrigerated container comprises of a pair of front and a pair of rear drain holes, an air exchanger, a pair of doors located at the rear of said container, and a refrigeration system, said method for fumigation comprising:

checking said container for any damaged areas;

if damaged areas found, then sealing said damaged areas with a means for sealing said damaged areas;

placing at least one fan within said container;

inserting through the air exchanger a gas introduction hose, then connecting said gas introduction hose to one of the fans earlier placed within said container or to the fan earlier placed in said container;

inserting through the air exchanger a plurality of reading lines for measuring the dispersion of fumigant within said container and an electrical line for powering said fans;

positioning said reading lines within said container:

sealing the air exchanger with a means for sealing the air exchanger;

plugging the front and rear drain holes with a means for plugging holes;

checking the temperature of the perishable to be fumigated:

determining the dosage of fumigant to be used in the fumigation process;

closing and securing the doors of the refrigerated cargo container;

releasing the fumigant required to fumigate through the gas introduction hose into said container;

checking with a gas or a halide detector the outside of said container for any fumigant leaks;

if leaks are discovered, then sealing the areas of said container found to have leaks with a means for sealing the areas found to have leaks;

re-checking with the gas or the halide detector the areas of the container that were discovered to have leaks;

if leaks are controlled, then conducting the fumigation process; and lastly, aerating the perishable fumigated for the required amount of time needed to clear the container of the fumigant used in the fumigation process.

14. The method for fumigating perishables within the refrigerated cargo container of claim 13, wherein the refrigerated container is refrigerating the perishable during the fumigation process.

15. The method for fumigating perishables within the refrigerated cargo container of claim 13, which further comprises conducting a pressure test of said refrigerated container prior to the application of the fumigant.

16. The method for fumigating perishables within the refrigerated cargo container of claim 15, wherein the refrigerated container is refrigerating the perishable during the fumigation process.

17. A method for fumigating perishables within a refrigerated cargo container, wherein said refrigerated container comprises of a pair of front and a pair of rear drain holes, a pair of doors located at the rear of said container, and a refrigeration system, said method for fumigation comprising:

checking said container for any damaged areas;

if damaged areas found, then sealing said damaged areas with a means for sealing said damaged areas;

placing at least one fan within said container;

clearing the pair of rear drain holes of said container;

inserting through one of the rear drain holes a gas introduction hose, then connecting said gas introduction hose to one of the fans earlier placed within said container or to the fan earlier placed in said container;

inserting through the other rear drain hole a plurality of reading lines for measuring the dispersion of fumigant within said container and an electrical line for powering said fans;

positioning said reading lines within said container;

sealing the rear drain holes with a means for sealing the rear drain holes;

plugging the front drain holes with a means for plugging holes;

checking the temperature of the perishable to be fumigated;

determining the dosage of fumigant to be used in the fumigation process;

closing and securing the doors of the refrigerated cargo container;

releasing the fumigant required to fumigate through the gas introduction hose into said container;

checking with a gas or a halide detector the outside of said container for any fumigant leaks;

if leaks are discovered, then sealing the areas of said container found to have leaks with a means for sealing the areas found to have leaks;

re-checking with the gas or the halide detector the areas of the container that were discovered to have leaks;

if leaks are controlled, then conducting the fumigation process; and lastly, aerating the perishable fumigated for the required amount of time needed to clear the container of the fumigant used in the fumigation process.

18. The method for fumigating perishables within the refrigerated cargo container of claim 17, wherein the refrigerated container is refrigerating the perishable during the fumigation process.

19. The method for fumigating perishables within the refrigerated cargo container of claim 17, which further comprises conducting a pressure test of said refrigerated container prior to the application of the fumigant.

20. The method for fumigating perishables within the refrigerated cargo container of claim 19, wherein the refrigerated container is refrigerating the perishable during the fumigation process.

* * * * *

US006403027C1

(12) EX PARTE REEXAMINATION CERTIFICATE (8309th)

United States Patent
Napoles et al.

(10) Number: US 6,403,027 C1
(45) Certificate Issued: Jun. 7, 2011

(54) METHOD FOR FUMIGATING PERISHABLES WITHIN A REFRIGERATED CARGO CONTAINER

(75) Inventors: Alexander Elias Napoles, Miami, FL (US); Alexander Alfred Napoles, Miami, FL (US)

(73) Assignee: Structural Tenting Corporation, Miami, FL (US)

Reexamination Request:
No. 90/009,571, Oct. 30, 2009

Reexamination Certificate for:
Patent No.: 6,403,027
Issued: Jun. 11, 2002
Appl. No.: 09/698,332
Filed: Oct. 27, 2000

(51) Int. Cl.
*A23L 3/34* (2006.01)
*A23L 3/3409* (2006.01)
*A61L 2/20* (2006.01)

(52) U.S. Cl. .................... 422/3; 422/1; 422/28; 422/32; 422/33; 422/37; 422/40; 426/327; 426/335; 62/78

(58) Field of Classification Search ........................ None
See application file for complete search history.

(56) References Cited

PUBLICATIONS

The term perishable(s) from Webster's II, New Riverside University Dictionary, p. 875, col. 1, 1988.*
Methyl Bromide Emergency Response Manual, Revision 2—Mar. 2000, Chemical Manufacturers Association.
Fumigation Guide, Great Lakes Chemical Corporation Agricultural Products, Apr. 1998, Great Lakes Chemical Corporation.
Directions for Use of the Product: Meth–O–Gas Q Commodity Fumigant for Quarantine/Regulatory Use Only, 2005, Great Lakes Chemical Corporation, Indiana.
Meth–O–Gas Products, Applicator Training Manual, Feb. 2000, Agricultural Products Business, Great Lakes Chemical Corporation.
Meth–O–Gas Q, Commodity Fumigant for Quarantine/Regulatory Use Only (Specimen Label), Great Lakes Chemical Corporation.
U.S. District Court—S.D. of Florida, Civil Docket for Case No. 1:02–cv–22288, *Structural Tenting Corporation et al* v. *Target Pest Control* (Printed Aug. 5, 2010/Miami, FL).
U.S. District Court—S.D. of Florida, Civil Docket for Case No. 1:09–cv–21285, *Structural Tenting Corporation et al* v. *Termite Doctor, LLC* (Printed Aug. 5, 2010/Miami, FL).

Motion and Memorandum to Stay Pending Decision on ReExamination of Patent and Exhibits [Case No. 1:09–cv–21285 /D.E.#14 Entered Sep. 24, 2009/Miami, FL].
Plaintiffs' Response in Opposition to Defendant's Motion and Memorandum to Stay Pending Decision . . . [Case No. 1:09–cv–21285 /D.E.#15 Entered Oct. 13, 2009/Miami, FL].
Defendant's Reply Memorandum in Support of its Motion and Memorandum to Stay Pending Decision on . . . [Case No. 1:09–cv–21285 /D.E.#16 Entered Oct. 20, 2009/Miami, FL].
Plaintiffs' Motion for Preliminary Injunction and Exhibits [Case No. 1:09–cv–21285 /D.E.#18 Entered Jan. 8, 2010/ Miami, FL].
Defendant's Memorandum in Opposition to Plaintiffs' Motion for Preliminary Injunction and Exhibits [Case No. 1:09–cv–21285 /D.E.#27 Entered Feb. 8, 2010/Miami, FL].
Plaintiffs' Reply to Defendant's Memorandum in Opposition to Plaintiffs' Motion . . . and Exhibits [Case No. 1:09–cv–21285 /D.E.#29 Entered Feb. 18, 2010/Miami, FL].
Joint Pretrail Stipulation [Case No. 1:09–cv–21285 /D.E.#40 Entered Jun. 11, 2010/Miami, FL].
Amendment to Joint Pretrial Stipulation [Case No. 1:09–cv–21285 /D.E.#63 Entered Jul. 1, 2010/Miami, FL].
Scheffrahn, Rudolf, H., Expert Report in the Matter of *Structural Tenting Corporation and Al Flex Exterminators Inc* vs. *The Termite Doctor LLC* / May 11, 2010 /Miami, FL.
Dow Agrosciences LLC, "Supplemental Labeling," Approved Jul. 15, 1994.
Scheffrahn, R.H., "Evaluation of Polymer Film Enclosures as Protective Barriers for Commodities from Exposure to Structural Fumigants," J Agric Food Chem 1990, 38, p. 904 only.
Dow Agrosciences, Structural Fumigation Manual, 1998, 276 pages, Dow Agrosciences LLC, Indianapolis, USA.
EPA's Stratospheric Protection Division, Methyl Bromide Alternative Case Study, part of EPA, 430–R–96–021, 10 Case Studies, Dec. 1996, vol. 2, U.S. EPA, Washington DC.

* cited by examiner

*Primary Examiner*—Dwayne C Jones

(57) ABSTRACT

A method for fumigation perishables within an existing refrigerated cargo container that does not require the refrigerated cargo container to be tented. The method uses the inherent characteristics of the cargo container to form the fumigation chamber environment. The method insures that the cargo container is fit for fumigation purposes, more specifically, that the refrigerated cargo container does not allow the escape of fumigant beyond the reasonable level allowed by the agency monitoring the fumigation process.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-20 is confirmed.

* * * * *